United States Patent
Ashton et al.

(10) Patent No.: US 6,319,489 B1
(45) Date of Patent: *Nov. 20, 2001

(54) AUTOPHOBIC HAIRSPRAY COMPOSITIONS

(75) Inventors: Melanie Ruth Ashton; Yvonne Christine Plant; Robert Polywka, all of Bebington (GB); Jean-Francois Rous, Le Meux Cedex (FR); John Temple, Bebington (GB)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,552

(22) Filed: Sep. 29, 1998

(30) Foreign Application Priority Data

Oct. 3, 1997 (GB) .................................................. 9721094

(51) Int. Cl.$^7$ ........................................................ A61K 9/12
(52) U.S. Cl. ................................. 424/47; 424/43; 424/45; 424/70.1; 424/70.11; 424/70.12; 424/70.15; 424/70.16; 424/70.19; 514/772.3
(58) Field of Search ................................. 424/43, 45, 47, 424/70.1, 70.11, 70.12, 70.15, 70.16, 70.19

(56) References Cited

U.S. PATENT DOCUMENTS 4,871,529    10/1989  Sramek .

FOREIGN PATENT DOCUMENTS

| 44 21 562 | 12/1995 | (DE) . |
|---|---|---|
| 590604 | 4/1994 | (EP) . |
| 0657157 | 6/1995 | (EP) . |
| 0705595 | 4/1996 | (EP) . |
| 93/03704 | 3/1993 | (WO) . |
| 93/03705 | 3/1993 | (WO) . |
| 95/04518 | 2/1995 | (WO) . |
| 95/06078 | 3/1995 | (WO) . |
| 97/15275 | 5/1997 | (WO) . |
| 97/33554 | 9/1997 | (WO) . |
| 97/46213 | 12/1997 | (WO) . |

OTHER PUBLICATIONS

International Search Report Application No. PCT/EP 98/05709 mailed Apr. 8, 1999.
Search Report under Section 17, Application No. GB 97/21094.2 dated Feb. 2, 1998.

Primary Examiner—Thurman K. Page
Assistant Examiner—P. E. McQueeney
(74) Attorney, Agent, or Firm—Matthew Boxer

(57) ABSTRACT

The use of at least 0.5% by weight water as an additive in a hairspray composition for the purpose of inducing or enhancing autophobic behavior in the hairspray composition.

11 Claims, No Drawings

AUTOPHOBIC HAIRSPRAY COMPOSITIONS

FIELD OF THE INVENTION

The present invention relates to hairspray compositions. More particularly the invention relates to autophobic hairspray compositions, ie those hairspray compositions which incorporate certain types of additive, such as a polymer, which cause the hairspray composition to contract upon drying, thereby improving the hold and sensory feel of the hairspray composition.

BACKGROUND AND PRIOR ART

Conventional hairspray formulations are ethanol based and therefore form highly wetting systems for hair. Coalescence of the aerosol droplets on the hair fibre and subsequent ethanol evaporation to leave solid polymer residue leads to a network of fibre-fibre bonds. The bonding arrangement holds the hairstyle in place. As is typical of a highly wetting system, the droplet morphology of the sprayed formulation on the hair is roughly symmetrical around the fibre with a contact angle of zero or near zero degrees.

There are, however, undesirable consequences in coating hair with polymer, manifesting in perceptions of sensory negatives such as stiffness, rigid feel, stickiness or unnatural feel.

U.S. Pat. No. 4,871,529 describes ethanol solvent-based hairspray compositions which employ a specific type of silicone copolyol which causes the hairspray composition to contract upon drying. This is described as an "autophobic effect" which causes large droplets of the composition to form, and produce larger juncture points between fibres. Localisation of deposits in this way is said to give stronger bonds and greater hold.

In U.S. Pat. No. 4,871,529 the autophobic effect is achieved by a specific type of silicone copolyol, SILWET® L-7602 (ex Union Carbide), a polyethylene oxide modified dimethylpolysiloxane in which the polyalkylene oxide groups are attached along the siloxane backbone through Si—C bonds. SILWET® L-7602 is representative of a class of "alkyl-pendant" type copolyol of the following general formula:

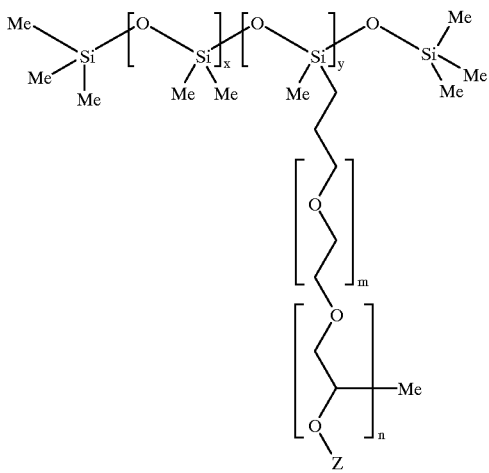

In SILWET® L-7602 specifically, n=0, m≧1 and Z is a methyl radical.

An "alkyl-pendant" silicone copolyol, for the purposes of the description, is a silicone copolyol in which polyalkyleneoxide groups are found scattered at various points, often randomly, along the length of the silicone backbone, from which they are pendant, resulting in "comb-like" structures.

SUMMARY OF THE INVENTION

We have investigated the mode of action of autophobic hairspray formulations on the actual hair fibre, as opposed to the glass slides employed for testing in U.S. Pat. No. 4,871,529. We have found, contrary to the teaching of U.S. Pat. No. 4,871,529 that it is not the molecular structure of the organosilicone copolymer as such that is critical to the autophobic effect. On the contrary, we have found that it is not even critical that the polymer is an organosilicone copolymer.

This was not appreciated in the prior art. Firstly, U.S. Pat. No. 4,871,529 the silicone copolyol SILWET® L-7602, is stated to be unique in that no other dimethicone copolyols tested rendered the compositions autophobic despite their diversity of molecular weight and properties.

We have found instead that autophobic character on the hair fibre is critically dependent on the inclusion of water in the hairspray formulation.

This is surprising since U.S. Pat. No. 4,871,529 advises the minimum amount of water in its systems, if it is present at all, stating that this tends to release the curls in the hair.

Advantageously, by the inclusion of water according to the present invention, it is possible to prepare particularly effective autophobic hairspray formulations which deliver durable hair hold yet reduced sensory negatives such as stiffness and unnatural feel.

Furthermore, the present invention offers greater formulational flexibility as regards the choice of silicone copolyol or other autophobic hairspray additive in the hairspray.

Moreover, with the advent of legislation concerning the volatile organic content of hairsprays, it is increasingly desirable to formulate systems with relatively high water content.

Accordingly in a first aspect the present invention provides the use of at least 0.5% by weight water as an additive in a hairspray composition for the purpose of inducing or enhancing autophobic behaviour in the hairspray composition.

In a second aspect the present invention provides the use of at least 0.5% by weight water as an additive in a hairspray composition for the purpose of inducing or enhancing autophobic behaviour in the hairspray composition, the composition comprising, in addition to the at least 0.5% by weight water:

a) from 0.5% to 10% by weight of a hairspray resin;

b) from 0 to 50% by weight of an aerosol propellant; and c) from 0.05% to 2% by weight of an autophobic hairspray surfactant or polymer, which is a surfactant or polymer which exhibits autophobic behaviour in conjunction with the at least 0.5% by weight water, and which is selected from the group consisting of:

(i) alkyl-pendant silicone copolyols of formula (I):

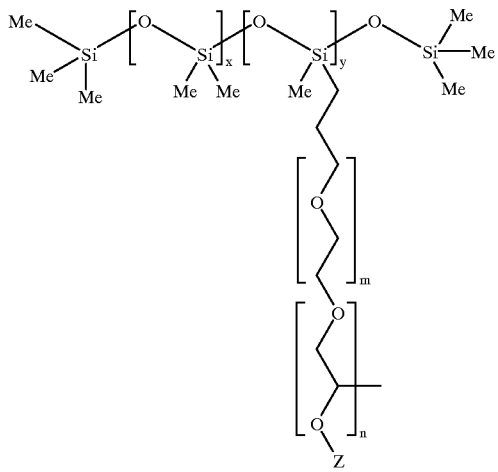

where m and n are integers of from 0 to 50, and x and y are integers chosen to give the copolyol a molecular weight of at least 600. Z is hydrogen or a C1-4 alkyl radical;

(ii) dimethicone copolyols of formula (II):

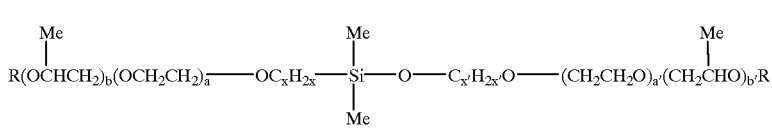

where n is an integer chosen to give the copolyol a molecular weight of at least 600;

x and x' are integers of from 1 to 12;

a,a',b,b' are integers of from 0 to 50, and R is hydrogen or a C1-4 alkyl radical;

(iii) polydimethicone copolyols of formula (III):

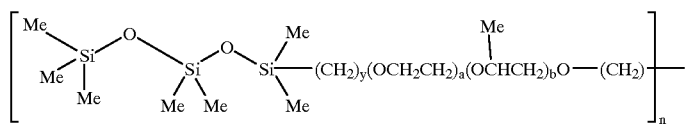

where x and n are integers chosen to give the copolyol a molecular weight of at least 500;

y is an integer of from 1 to 12, and a and b are integers of from 0 to 50;

(iv) alkyl ethoxylates; and (v) fluorosurfactants.

In a third aspect the invention provides a hairspray composition comprising:

a) from 0.5% to 10% by weight of a hairspray resin;

b) from 0 to 50% by weight of an aerosol propellant; and c) at least 0.5% by weight water; and d) from 0.05% to 2% by weight of a an autophobic hairspray surfactant or polymer selected from the group consisting of dimethicone copolyols of formula (II) as defined above, polydimethicone copolyols of formula (III) as defined above, alkyl ethoxylates, and fluorosurfactants.

DETAILED DESCRIPTION OF THE INVENTION

Hairspray Resin

The hairspray resins employed in compositions of the present invention should be capable of forming a film and holding the hair of the user in place after evaporation of the volatile components of the hairspray composition.

Hairspray resins are well known articles of commerce and many such resinous polymers are available commercially which contain moieties which render the polymers cationic, anionic, amphoteric or nonionic in nature. To provide optimum sprayability, the polymers employed in hairspray compositions typically range in number average molecular weight of from 5,000 to 100,000 with 10,000 to 50,000 being more preferred. For pump spray use, hairspray resins in the range of number average molecular weight 10,000 to 50,000 are typically employed.

The amount of the resin may range from 0.5 to 10%, preferably 1.5 to 6% by weight of the hairspray composition.

Examples of anionic hairspray resins are copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1:1) wherein such copolymers are 50% esterified with a saturated alcohol containing from 1 to 4 carbon atoms such as ethanol or butanol; and acrylic copolymers, terpolymers, etc., containing acrylic acid or methacrylic acid as the anionic radical-containing moiety and esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerised terpolymer of methacrylic acid, n-butyl acrylate and ethyl acrylate (e.g., in a weight percent ratio of 31:42:27, respectively).

Another specific example is Ultrahold® 8 (CTFA-Cosmetic, Toiletries and Fragrance Association designation of Acrylate/Acrylamide Copolymer).

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hairspray resin is Amphomer® sold by the National Starch and Chemical Corporation.

Examples of nonionic hairspray resins are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 sold by ISP (formerly GAF Corporation) under the tradename PVP K-90 and those having an average molecular weight of about 1,000,000 sold under the trademark of PVP K-120.

Examples of cationic hairspray resins are copolymers of amino-functional acrylate monomers such as lower alkyl aminoalkyl acrylate or methacrylate monomers such as dimethylaminoethyl methacrylate with compatible monomers such as N-vinylpyrrolidone, vinyl caprolactam, or alkyl methacrylates such as methyl methacrylate and ethyl methacrylate and alkyl acrylates such as ethyl acrylate and n-butyl acrylate.

Cationic polymers containing N-vinylpyrrolidone are commercially available from ISP Corporation such as those sold under the trademarks of Copolymer 845 and Copolymer 937 (copolymers of N-vinylpyrrolidone and t-butylaminoethyl methacrylate of average molecular weight about 1,000,000) and Gafquat® 755 and 755N (quaternary ammonium polymers formed by the reaction of dimethyl sulfate and a copolymer of N-vinylpyrrolidone and dimethylaminoethyl methacrylate of average molecular weight about 1,000,000).

With certain of the resins it may be necessary to neutralise some acidic groups to promote solubility/dispersibility. Examples of suitable neutralising agents include 2-amino-2-methyl-1, 3-propanediol (AMPD); 2-amino-2-ethyl-1,3-propanediol AEPD); 2-amino-2-methyl-1-propanol (AMP); 2-amino-1-butanol (AB); monoethanolamine (MEA)-; diethanolamine (DEA); triethanolamine (TEA); monoisopropanolamine (MIPA); diisopropanol-amine (DIPA); triisopropanolamine (TIPA); and dimethyl stearamine (DMS). If the hairspray resin contains carboxyl groups, a long chain amine neutralising agent such as lauramidopropyl dimethylamine may be employed, as is described in U.S. Pat. No. 4,874,604. Amounts of the neutralising agents will range from about 0.001 to about 10% by weight.

Water

Compositions of the present invention include water, which we have found to be critical to the occurrence of the autophobic effect. Below 0.5% water content, no appreciable effect is encountered.

The upper water content limit is not critical to the present invention, but in general is governed by the tendency of the hairspray formulation to impart a sticky feel to the hair if the level of water is too high. However, with the advent of legislation concerning the volatile organic content of hairsprays, it is increasingly desirable to formulate systems with relatively high water content. A water content of up to 30%, even 45–55%, by weight, may therefore be appropriate.

Typical water levels for an ethanol-based aerosol fixing spray are from 2 to 10%, preferably 2 to 6% by weight. For "style creating" sprays a higher water content is generally preferred, and the water content is typically 5 to 15%, preferably 5 to 10% by weight.

It is not clear how the use of water according to the present invention induces or enhances the autophobic effect. Whilst not wishing to be bound by any theory, it is believed that the presence of water results in interfacial changes involving the autophobic hairspray polymer.

Autophobic Hairspray Surfactant or Polymer

Illustrative alkyl-pendant silicone copolyols of formula (I) as referred to above are described in U.S. Pat. No. 4,871,529, e.g. the silicone copolyol SILWET® L-7602. In U.S. Pat. No. 4,871,529 the silicone copolyol SILWET® L-7602 is stated to be unique in that no other dimethicone copolyols tested rendered the compositions autophobic. The present inventors have found, contrary to this, that autophobic character in hairspray compositions is not unique to SILWET® L-7602.

Dimethicone copolyols of formula (II) referred to above are sometimes designated as "ABA" type copolymers, due to the presence of alternating polyalkylene oxide and silicone blocks. These are of different character to SILWET® L-7602 since they are not "alkyl-pendant" type copolymers.

Similarly, polydimethicone copolyols of formula (III) referred to above are sometimes designated as (AB)n type copolymers. These are also not "alkyl-pendant".

The molecular weight of the copolyols of formulae (II) and (III) suitably ranges from 500 to 50,000.

Suitable dimethicone copolyols of formula (II) are SILSOFT®900, sold by OSi Specialties, having a molecular weight of about 2000, with R being hydrogen and a being 0, and the materials sold by Goldschmidt as TEGOPREN® 3012 and 5830 respectively.

Suitable polydimethicone copolyols of formula (III) are those described in U.S. Pat. No. 4242466. Illustrative is the material sold by OSi Specialties as SILSOFT® 487, having a molecular weight of about 150,000, with a and b both greater than 0.

Particularly surprisingly, the present inventors have found that it is not even critical that the autophobic hairspray polymer is an organosilicone copolymer. Certain surfactants have also been shown to exhibit this behaviour in conjunction with water.

Examples of alkyl ethoxylates which have been found to exhibit autophobic behaviour in compositions of the present invention are those of general formula (IV):

$$C_nH_{2n+1}(OCH_2CH_2)_xOR \qquad (IV)$$

where n is an integer of from 5 to 20, preferably from 8 to 18, most preferably 12 to 14;

x is an integer of from 3 to 50, preferably from 3 to 30; and

R is hydrogen or a $C_{1-4}$ alkyl group, e.g. methyl. Preferably R is hydrogen.

Illustrative are GENAPOL® C-250, (ex Hoechst Celanese), which is coconut fatty alcohol (C8–C18, mainly C12–C14) ethoxylated with 25 moles of ethylene oxide, and DOBANOL® 91-5 (ex Shell), which is C9–C11 alcohol ethoxylated with 5 moles of ethylene oxide.

Fluorosurfactants are surfactants in which the hydrophobic segment of the molecule contains fluorine. At least one hydrogen atom in the hydrophobic segment contains fluorine. The hydrophobe can be fully fluorinated (perfluorinated) or partially fluorinated. As with conventional surfactants, fluorosurfactants can be classified into four types: anionic, cationic, amphoteric and nonionic. Their structural features are described in the book "Fluorinated Surfactants—Surfactant Science Series Vol.50" by Eric Kissa, Marcel Dekker Inc., 1994, Chapter 1.

An example of a fluorosurfactant which has been found to exhibit autophobic behaviour in compositions of the present invention is the material sold by Dow/3M as L13564, of formula (V):

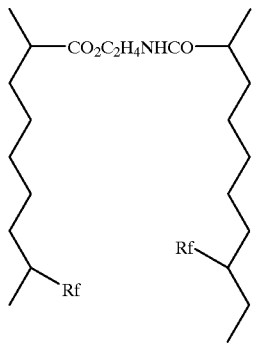

Where $R_f$ is a fluorine containing hydrophobe.

Product Form

Hairspray compositions of the present invention can be formulated as sprays in aerosol or non-aerosol forms, and so can be dispensed from containers which are propellant—charged aerosol containers, or alternatively pump spray containers operated without any propellant.

When the hairspray compositions are to be dispensed from a pressurised aerosol container, an aerosol propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than the hairspray concentrate so that pure propellant is not emitted from the container. Examples of suitable propellants include dimethyl ether, propane, n-butane and isobutane, used singly or admixed. Other examples of propellants are nitrogen, carbon dioxide and compressed air.

The amount of the propellant gases is governed by normal factors well known in the aerosol art. For hairsprays the level of propellant is generally from about 3 to about 50%, preferably from about 5 to about 45%, optimally about 35 to 45% of the total composition.

Optional Ingredients

Compositions of this invention may contain any other ingredient normally used in hairsprays. These other ingredients may include antifoam agents, proteins, moisturising agents, antioxidants, fragrances, antimicrobials and sunscreens. Each of these ingredients will be present in an amount effective to accomplish its purpose.

Packaging

Hairspray formulations of the present invention may, if desired, be packaged in a pump spray container operated without any propellant. Otherwise, the composition may be charged into a suitable pressurisable container which is sealed and then charged with propellant according to conventional techniques.

The following examples will more fully illustrate the embodiments of this invention.

All parts, percentages and proportions referred to are by weight unless otherwise indicated.

| | EXAMPLE (WEIGHT %) | | | | | | | | |
|---|---|---|---|---|---|---|---|---|---|
| COMPONENT | 1 | 2 | 3 | 4 | 5 | 6 | 7 | 8 | 9 |
| Water | 10 | 10 | 3 | 3 | 10 | 10 | 3 | 3 | 10 |
| Amphomer[1] | 2.5 | — | 2.5 | — | — | — | 2.5 | — | 2.5 |
| Luvimer[2] | — | 2.5 | — | 2.5 | 2.5 | 2.5 | — | 2.5 | — |
| Silsoft 487[3] | 1 | 0.25 | — | — | — | — | — | — | — |
| Silsoft 900[4] | — | — | 0.15 | — | — | — | — | — | — |
| Y12700[5] | — | — | — | 1 | 0.25 | — | — | — | — |
| F178-03[6] | — | — | — | — | — | 1 | 1 | — | — |
| F178-05[7] | — | — | — | — | — | — | — | 0.25 | 0.25 |
| F178-09[8] | — | — | — | — | — | — | — | — | — |
| F178-21[9] | — | — | — | — | — | — | — | — | — |
| F178-28[10] | — | — | — | — | — | — | — | — | — |
| Tegopren 3012[11] | — | — | — | — | — | — | — | — | — |
| Tegopren 5830[12] | — | — | — | — | — | — | — | — | — |
| PCL Liquid | | | | | 0.0077 | | | | |
| Perfume | | | | | 0.15 | | | | |
| D-Panthenol | | | | | 0.15 | | | | |
| Ethanol | | | | | BALANCE | | | | |

| COMPONENT | 10 | 11 | 12 | 13 | 14 | 15 | 16 | 17 | 18 | 19 |
|---|---|---|---|---|---|---|---|---|---|---|
| Water | 10 | 10 | 3 | 3 | 3 | 10 | 10 | 10 | 3 | 3 |
| Amphomer[1] | 2.5 | — | 2.5 | — | — | — | 2.5 | — | 2.5 | — |
| Luvimer[2] | — | 2.5 | — | 2.5 | 2.5 | 2.5 | — | 2.5 | — | 2.5 |
| Silsoft 487[3] | — | — | — | — | — | — | — | — | — | — |
| Silsoft 900[4] | — | — | — | — | — | — | — | — | — | — |
| Y12700[5] | — | — | — | — | — | — | — | — | — | — |
| F178-03[6] | — | — | — | — | — | — | — | — | — | — |
| F178-05[7] | — | — | — | — | — | — | — | — | — | — |
| F178-09[8] | 0.25 | 1 | — | — | — | — | — | — | — | — |
| F178-21[9] | — | — | 0.25 | 1 | — | — | — | — | — | — |
| F178-28[10] | — | — | — | — | 1 | 0.25 | — | — | — | — |
| Tegopren 3012[11] | — | — | — | — | — | — | 0.25 | 1 | — | — |

-continued

| | EXAMPLE (WEIGHT %) | | | | | | | | | |
|---|---|---|---|---|---|---|---|---|---|---|
| Tegopren 5830[12] | — | — | — | — | — | — | — | — | 0.25 | 1 |
| PCL Liquid | | | | | 0.0077 | | | | | |
| Perfume | | | | | 0.15 | | | | | |
| D-Panthenol | | | | | 0.15 | | | | | |
| Ethanol | | | | | BALANCE | | | | | |

| | EXAMPLE (WEIGHT %) | | | |
|---|---|---|---|---|
| COMPONENT | 20 | 21 | 22 | 23 |
| Water | 10 | 3 | 10 | 10 |
| Amphomer[1] | 2.5 | — | 1 | 0.25 |
| Luvimer[2] | — | 2.5 | — | — |
| L13564[13] | 0.25 | 0.25 | — | — |
| GENAPOL C250[14] | — | — | 1 | — |
| DOBANOL 91-5[15] | — | — | — | 0.25 |
| PCL Liquid | | | 0.0077 | |
| Perfume | | | 0.15 | |
| D-Panthenol | | | 0.15 | |
| Ethanol | | | BALANCE | |

1) Octylacrylamide/acrylates/butylaminoethyl methacrylate copolymer, ex. National Starch.
2) t-butyl acrylate/ethyl acrylate/methacrylic acid copolymer, ex BASF.
3) Polydimethicone copolyol, (AB)n type ex. OSi Specialities.
4) Propoxylated dimethicone copolyol, (ABA) type, ex. Osi Specialities.
5) Ethoxylated dimethicone copolyol, (ABA) type, ex OSi Specialities.
6)–10) Dimethicone copolyols, (ABA) type, ex Nihon Uniker.
11),12) Dimethicone copolyols, (ABA) type, ex Goldschmidt.
13) Fluorosurfactant, ex Dow/3M
14) Coconut fatty alcohol with 25 moles ethoxylate
15) C9–C11 alcohol with 5 moles ethoxylate Evaluation for Auto-phobic Behaviour U.S. Pat. No. 4,871,529 (col. 7, lines 33 to 68) describes a test for evaluating the autophobic effect in which a film of the hairspray composition is spread over the surface of a glassslide and its character on drying observed.

Hair fibres, however, have different surface properties to glass slides—we have found that a more accurate characterisation of autophobic systems is obtained through optical microscopy studies of composition behaviour on the hair fibre itself. Conventional systems display high wetting of hair fibres. In these systems, solid (including hairspray resin) deposited in fibre-fibre junctions is significantly spread along the fibres from the centre of the junction along the length of the fibres. In contrast, autophobic systems appear to localise deposition at fibre-fibre junctions, with a reduced coating of those fibre regions external to the junctions. This is consistent with the deposit being formed from a poorly wetting system, that is, the liquid makes a high contact angle with the fibre. The high contact angle droplet morphology of the dried autophobic system on crossed hair fibres can be viewed by magnifying lens. The formulations of Examples 1–23 were assessed for autophobic behaviour by the following method:

Each Example to be tested was pressurised in an aluminium can with 35% CAP 40 (hydrocarbon propellant) to form a hairspray.

Assessment of the spray was made by spraying onto Spanish hair in good condition. Hair fibres were mounted onto brass frames using sticky tape in a crossed formation. The crossed fibres were sprayed, with the can in an upright position, from a distance of 20 cm for a 1–2 second burst.

The droplets of hairspray which had deposited onto the fibre were then imaged using a camera fitted with a X4 magnifying lens. The camera was linked to a video recorder and all experiments recorded and archived. The droplets were monitored until dried down and more specifically for between 30 seconds and 5 minutes.

The autophobic effect was assessed by observing for shape change which demonstrates that the hairspray is "rolling up" on the hair. Initially when the drop lands on the hair fibre the droplet is symmetrical and has zero contact angle. This initial behaviour is also typical of conventional systems. However, for conventional systems, the droplet remains symmetrical on drying down and eventually, when dry, leaves an even coating all over the fibres. Whereas for autophobic systems, after about 30 seconds the droplet starts changing shape, it becomes unsymmetrical and the contact angle increases.

The results of the above assessment were that examples 1–23 all exhibited high contact angle droplet morphologies characteristic of autophobic systems.

What is claimed is:

1. A hairspray composition comprising in addition to at least 5% by weight water:
   a) from 0.5% to 10% by weight of a hairspray resin;
   b) from 0 to 50% by weight of an aerosol propellant; and
   c) from 0.05% to 2% by weight of an autophobic hairspray surfactant or polymer, which is a surfactant or polymer which exhibits autophobic behaviour in conjunction with at least 0.5% water, and which is selected from the group consisting of:
      (i) dimethicone copolyols of formula (I):

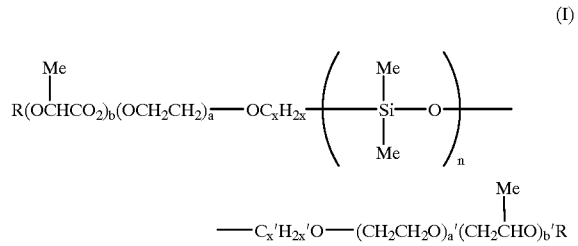

where n is an integer chosen to give the copolyol a molecular weight of at least 600;
x and x' are integers of from 1 to 12;
a, a', b, b' are integers of from 0 to 50, and R is hydrogen or a C1-4 alkyl radical; and (ii) polydimethicone copolyols of formula (II):

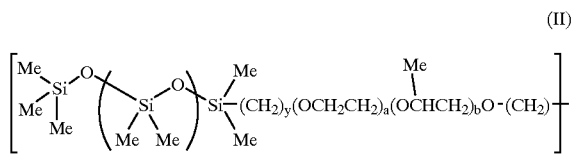

where x and n are integers chosen to give the copolyol a molecular weight of at least 500;

y is an integer of from 1 to 12, and a and b are integers of from 0 to 50.

2. A hair spray composition comprising:
   a) from 0.5% to 10% by weight of a hairspray resin;
   b) from 0% to 50% by weight of an aerosol propellant; and
   c) at least 0.5% by weight water; and
   d) from 0.05% to 2% by weight of an autophobic hairspray surfactant or polymer selected from the group consisting of dimethicone copolyols of formula (I) and polydimethicone copolyols of Formula (II).

3. A composition according to claim 2 in which the autophobic hairspray surfactant or polymer is a dimethicone copolyol of formula (II) with R being hydrogen and a and a' each being 0.

4. A composition according to claim 2 in which the hairspray resin is present in an amount of from 1.5 to 6% by weight.

5. A composition according to claim 2 in which water is present in an amount of from 2 to 15% by weight.

6. A composition according to claim 2 which is formulated as a spray in aerosol form and which further comprises from 3 to 50% of an aerosol propellant.

7. A composition according to claim 6, in which the aerosol propellant is selected from the group consisting of dimethyl ether, propane, n-butane, isobutane, and mixtures thereof.

8. A composition according to claim 2 which is formulated as a spray in non-aerosol form and which is packaged in a pump spray container operated without any aerosol propellant.

9. A hairspray composition comprising:
   a.) from 0.5% to 10% by weight of a hairspray resin;
   b.) from 0 to 50% by weight of an aerosol propellant;
   c.) at least 0.5% by weight water, and
   d.) from 0.05 to 2% by weight of an autophobic hairspray surfactant or polymer.

10. A composition according to claim 1, wherein said composition exhibits high contact angle droplet morphology.

11. A method for inducing or enhancing autophobic behavior in hair which comprises applying to said hair a composition according to claim 1.

* * * * *